(12) United States Patent
Okada et al.

(10) Patent No.: US 6,235,225 B1
(45) Date of Patent: May 22, 2001

(54) PROCESS FOR PRODUCING BIOCOMPATIBLE IMPLANT MATERIAL

(75) Inventors: Kohji Okada; Tsunetoshi Okura; Jun Sugimoto; Masahiko Okuyama, all of Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/635,500

(22) Filed: Aug. 9, 2000

(30) Foreign Application Priority Data

Aug. 10, 1999 (JP) .................................................. 11-226675

(51) Int. Cl.[7] .............................. B22F 5/10; B29C 65/00
(52) U.S. Cl. .................................... 264/44; 264/43; 419/2
(58) Field of Search ................................. 264/42, 43, 44, 264/628; 419/2

(56) References Cited

U.S. PATENT DOCUMENTS

| 4,308,064 | 12/1981 | Takami et al. ....................... 501/135 |
| 4,371,484 | 2/1983 | Inukai et al. ........................... 264/44 |
| 4,376,168 | 3/1983 | Takami et al. ........................... 501/1 |
| 4,610,692 * | 9/1986 | Eitenmuller et al. .................. 623/16 |
| 4,654,314 * | 3/1987 | Takagi et al. ........................... 501/82 |
| 4,751,013 * | 6/1988 | Kaarmann et al. ................... 252/69.2 |
| 4,963,145 | 10/1990 | Takagi et al. ........................... 606/76 |
| 5,549,123 | 8/1996 | Okuyama et al. ................... 128/898 |
| 5,679,294 * | 10/1997 | Umezu et al. ......................... 264/44 |

FOREIGN PATENT DOCUMENTS

| 0 267 624 | 5/1988 | (EP) . |
| 60-50744 | 11/1985 | (JP) . |
| 3-131580 | 6/1991 | (JP) . |

* cited by examiner

*Primary Examiner*—Christopher A. Fiorilla
(74) *Attorney, Agent, or Firm*—Sughrue, Mion, Zinn, Macpeak & Seas, PLLC

(57) ABSTRACT

A process for producing a biocompatible implant material which can be suitably shaped into a variety of forms. A binder is added to a mixture of hydroxylapatite powder and calcium phosphate glass frit (5 wt. %), to thereby prepare a slurry, and the resultant slurry is granulated, to prepare spherical raw material granules. Separately, spherical polyisobutyl methacrylate particles are prepared, and the particles are dry-mixed with the above-prepared granules, to thereby obtain a powder mixture. The powder mixture is compacted using a mold press, to thereby form a cuboid sample. The resultant compact is heated in a drier at 170° C. for three hours, to thereby melt spherical polyisobutyl methacrylate particles. Thereafter, the compact is allowed to cool, to thereby bind the raw material granules together via the polyisobutyl methacrylate that solidifies after melting. After the compact is allowed to cool, the compact is subjected to shaping by use of a copy machining machine and also to drilling. Thereafter, the compact is heated at a rate of 300° C. hour, and fired at 1,250° C. for three hours, to thereby produce a biocompatible implant material.

7 Claims, 2 Drawing Sheets

PROCESS FOR PRODUCING BIOCOMPATIBLE IMPLANT MATERIAL

BACKGROUND OF THE INVENTION

1. Field of the Invention

The present invention relates to a process for producing a biocompatible implant material. The biocompatible implant material produced by the inventive process is adapted for use as a prosthetic material for artificial bone in clinical fields such as orthopedic surgery, plastic surgery, brain surgery, oral surgery, and dental surgery.

2. Description of the Related Art

Conventionally, metallic material has been employed as a biocompatible implant material, but in recent years, ceramic material has become of interest and has been practically employed in consideration of biocompatibility. Particularly, it is known that calcium phosphate compounds have excellent biocompatibility, and that sintered products of these compounds can be chemically bound to bone or can substitute for bone.

Japanese Patent Publication (kokoku) No. 60-50744 discloses a process for producing sintered calcium phosphate which has excellent biocompatibility and high strength, in which powder predominantly comprising calcium phosphate (the atomic ratio of calcium to phosphorous is 1.4–1.75) is mixed with alkaline earth metal oxide-phosphoric acid frit such that the amount of the frit is 0.5–15 wt. % on the basis of the entirety of sintered calcium phosphate after firing; and the resultant mixture is fired. According to this process, a biocompatible implant material having excellent biocompatibility and high strength can be produced. When the thus-produced biocompatible implant material is implanted into the body, the material is chemically bound to osseous tissue and exhibits excellent effects, since the material has high strength and therefore is rarely broken. However, this material does not permit bone cells to enter therein, and therefore bone cells are not allowed to grow satisfactorily, requiring a prolonged period of time before binding of the material to the bone tissue.

Meanwhile, a porous implant material has lower strength than that of a dense material, but greater biocompatibility. Bone cells easily enter a porous material; particularly, a material comprising large pores having a size of some tens to some hundreds of $\mu$m. Conventionally, there are processes for producing a porous material; for example, a process in which a combustible pore-forming material such as an organic substance or carbon is introduced into a raw material, and a process in which a foaming agent is incorporated into a raw material. Such processes have been employed for producing bricks, and when these processes are applied to calcium phosphate material, a porous implant material can be prepared.

Although a porous biocompatible implant material produced by such a conventional process comprises large pores having a size of approximately 100 $\mu$m, inter-pore connection of the material is not satisfactory. Therefore, it is often observed that bone cells do not grow into the pores of such a material, and that the material has poor properties for the growth of bone. In addition, such a conventionally produced porous material has considerably low strength, and thus particles constituting the material may fall, or the material may break when it is touched or rubbed by the fingers. Namely, handling the material is difficult, and operation efficiency of the material is considerably poor when employed in a bone prosthesis operation.

In order to solve the above-described drawbacks, Japanese Patent Application Laid-Open (kokai) No. 7-194688 discloses a process in which raw material powder having a mean particle size of 5 $\mu$m or less is formed into raw material granules having a particle size of 10–800 $\mu$m; the granules are mixed with combustible particles having a size of 2–1,600 $\mu$m; the mixture is compacted at a pressure of 1–100 kg/cm$^2$; and the compacted product is fired. According to this process, a porous biocompatible implant material can be produced which comprises particle-linking structures in which particles of 10–800 $\mu$m are linked together, and spaces through which pores of 2–800 $\mu$m three-dimensionally connect with one another between the above structures. Unlike a conventional porous material, the porous biocompatible implant material has excellent inter-pore connection and comprises large pore-linkage portions. Therefore, the porous biocompatible implant material allows bone cells to enter the material very easily and thus exhibits excellent biocompatibility.

Problems to be Solved by the Invention

Conventionally, material powder is compacted to obtain a compact of a block-like shape having an appropriate size, and the compact is then fired to thereby produce a porous biocompatible implant material as a product. The thus-produced product is appropriately shaped into an arbitrary form upon operation so as to match the form of the portion in which the material is to be implanted. However, in order to meet any possible requirement of orthopedic surgery or plastic surgery, a product must be produced having a form which matches a lost portion of bone; i.e., a product which has been shaped into an arbitrary form. For production of ceramics, a process may be employed in which a compacted product is prepared, the product is shaped, and the shaped product is fired. For example, Japanese Patent Application Laid-Open (kokai) No. 7-194688 discloses a process in which raw material granules are mixed with a combustible substance, the mixture is compacted at relatively low pressure, and the compacted product is fired, to thereby produce a final product. However, the compacted product has low strength and is brittle before firing, and thus the product is difficult to shape into an arbitrary form.

SUMMARY OF THE INVENTION

In view of the foregoing, an object of the present invention is to provide a process for producing a biocompatible implant material, which process is suitable for production of biocompatible implant materials having a variety of forms.

In order to solve the aforementioned problems, the present invention provides a process for producing a biocompatible implant material, which comprises:

a compacting step of compacting a mixture of sinterable raw material granules and thermoplastic combustible particles to thereby obtain a compact;

a binding step of heating the compact to the softening point of the thermoplastic combustible particles or higher to thereby thermally deform or melt the particles between the raw material granules, and then cooling the compact to thereby solidify the deformed or melted particles, for binding the raw material granules together;

a shaping step of shaping the bound compact into an arbitrary form; and a final step of burning out the thermoplastic combustible particles which are present between the raw material granules and for sintering the granules, to thereby produce a porous biocompatible implant material.

DETAILED DESCRIPTION OF THE INVENTION

Figure 1:
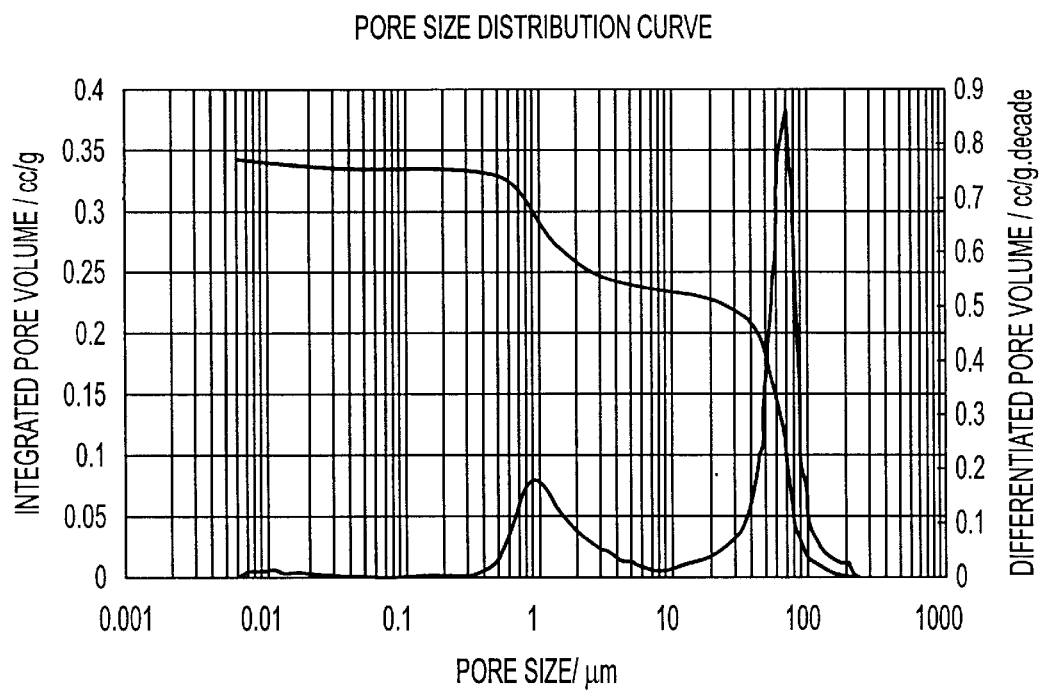
FIG. 1 is a chart showing the pore size distribution curve of the biocompatible implant material of Example 1 (Sample No. 16).

In the binding step of the process of the present invention, a compact, which is obtained by compacting a mixture of sinterable raw material granules and thermoplastic combustible particles, is heated to the softening point of the thermoplastic combustible particles or higher to thereby thermally deform or melt the particles. The compact is then cooled to thereby solidify the deformed or melted thermoplastic combustible particles, so as to bind the raw material granules together. As a result, the compact after the binding step has very high strength as compared with the compact before binding. Therefore, falling of the raw material granules is not observed, the compact can be handled with ease, and chips are not produced in the compact even when the compact is shaped by cutting or drilling in a subsequent shaping step. After the compact is shaped into an arbitrary form in the shaping step, a porous biocompatible implant material is produced in the final step. As described above, in the present invention, the compact after the binding step can be shaped into an arbitrary form which matches a lost portion of bone. Namely, in the present invention, a porous biocompatible implant material having an arbitrary form can be produced.

The heating temperature in the binding step is next described in detail. The heating temperature varies with the species of thermoplastic combustible resin which constitutes the thermoplastic combustible particles. Namely, the heating temperature is appropriately determined in accordance with the properties of the thermoplastic combustible resin. For example, in the case in which a thermoplastic combustible resin is employed whose area of contact with the raw material granules increases when thermally deformed, heating is carried out within a temperature range between the softening point and the melting point of the resin. In this case, the heating temperature is preferably a temperature which is in the vicinity of the melting temperature of the resin. For example, the heating temperature preferably falls within a temperature range from the mid point between the softening point and the melting point to the melting point. Alternatively, the heating temperature is set to be not lower than 80% of the melting point but lower than the melting point. In the case in which a thermoplastic combustible resin is employed which is solidified when cooled after thermal melting, heating may be carried out at the melting point of the resin, or at a temperature higher than the melting point, so long as the molten resin does not flow out from a compact. Specifically, when polybutyl methacrylate such as polyisobutyl methacrylate or poly-n-butyl methacrylate is employed as a material constituting the thermoplastic combustible particles, the heating temperature is preferably 120–190° C. When polyethylene such as low density polyethylene or medium density polyethylene is employed as a material constituting the thermoplastic combustible particles, the heating temperature is preferably 100–180° C.

In the binding step of the process of the present invention, the heating temperature of the compact is preferably set at a temperature at which the melted thermoplastic combustible particles do not melt and flow out from the compact. When the heating temperature is excessively high, liquid formed of melted thermoplastic combustible particles has an excessively low viscosity and flows out from the compact. As a result, the amount of a thermoplastic combustible component which is present between raw material granules becomes insufficient, and thus it is difficult to obtain a compact exhibiting sufficient strength after the binding step.

In the compacting step of the process of the present invention, the pressure for compacting a powder mixture is preferably determined such that the raw material granules do not break and the granules are packed with the substantially highest density. This is also known as the "closest packing" technique in which large grains and small grains are used in a computed mixing ratio so that spaces made by the large grains are filled by the small grains. Furthermore, spaces still remaining between the large and small grains are filled by much smaller grains. In such manner, "closest packing" is achieved, or the grains are "closely packed". As used herein, the term "breakage of raw material granules" refers to, for example, a case in which raw material granules formed of agglomerated particles are crushed into particles. The term "breakage of raw material granules" does not refer to a deformation of raw material granules to such a degree that the area of mutual contact between the raw material granules is increased due to deformation (such deformation is rather preferable in consideration of the strength of a compact). In the final step of the process, after the thermoplastic combustible component which is present between raw material granules is burned out, portions from which the component is lost form pores, and pores adjacent to one another connect three-dimensionally to thereby form spaces. Since spaces having a very small cross-sectional area are not formed, bone cells very easily enter a biocompatible implant material comprising such spaces, and the material exhibits excellent biocompatibility. In the process, spaces having a very small cross-sectional area are not formed, since relatively large spaces are present between raw material granules and the thermoplastic combustible particles during the compacting step. On the other hand, when raw material granules break during the compacting step, powder may enter between the raw material granules and the thermoplastic combustible particles, with the result that only small spaces are present therebetween, and thus spaces having a very small cross-sectional area tend to form during the final step. As a result, an implant material exhibiting poor biocompatibility is produced.

When the raw material granules and thermoplastic combustible particles have a generally spherical particulate form, the granules and the particles are closely packed or brought into contact with one another. Therefore, when the granules and the particles are fired, intraparticle binding or interparticle binding (a bond formed from such binding may be referred to as a "neck") tends to form, and thus the fired compact has high strength. The resulting, finally produced biocompatible implant material can advantageously be handled with ease.

In the compacting step of the process of the present invention, preferably, a mixture of raw material granules (granule size: 10–800 $\mu$m) which are formed from powder having a mean particle size of 5 $\mu$m or less and thermoplastic combustible particles (particle size: 2–1,600 $\mu$m) is compacted at a pressure of 1–200 kg/cm$^2$. In this case, raw material granules rarely break during the compacting step, and thus the finally produced biocompatible implant material comprises spaces through which pores having a relatively large size (approximately 2–800 $\mu$m) connect three-dimensionally. In addition, spaces having a very small cross-sectional area are not formed, and a biocompatible implant material comprising such spaces exhibits excellent biocompatibility.

Granules having a diameter of up to 100 $\mu$m may be prepared by a spray drying method. Granules having a diameter of more than 100 $\mu$m may be prepared by pressing the granules thus formed into a compact and breaking or fracturing the compact into pieces.

In the present invention, the mean particle size of the raw material powder is set at 5 $\mu$m or less, for the reasons described below. When the mean particle size is in excess of 5 $\mu$m, necks tend not to form, and thus it is difficult to form a porous structure in which the particles are bound to one another. As a result, for example, particles may fall from an implant material which is a final product, and thus a biocompatible implant material of desired strength may not be produced. When the mean particle size of raw material powder is 3 $\mu$m or less, the resulting biocompatible implant material has higher strength, which is more preferable. The size of raw material granules is set at 10–800 $\mu$m, for the reasons described below. When the size of the raw material granules is less than 10 $\mu$m, it is difficult to form the preferred pores, and thus the resultant biocompatible implant material has poor biocompatibility, whereas when the size is in excess of 800 $\mu$m, the resultant biocompatible implant material has deteriorated strength and the material cannot be handled with ease. On the other hand, the size of the thermoplastic combustible particles is set at 2–1,600 $\mu$m, for the reasons described below. When the size is less than 2 $\mu$m, only pores are formed in large amounts, and spaces having a sufficient cross-sectional area cannot be formed, whereas when the size is in excess of 1,600 $\mu$m, pores having a very large size are formed, and thus the resultant biocompatible implant material tends to have low strength. In the present invention, the pressure for compacting is set at 1–200 kg/cm$^2$, for the reasons described below. When the pressure is less than 1 kg/cm$^2$, it is difficult to compact raw material granules or thermoplastic combustible particles into a close-packed form or a similar form, and necks tend not to grow even when the granules or the particles are fired. Thus, a biocompatible implant material of low strength tends to be produced. In contrast, when the pressure is in excess of 200 kg/cm$^2$, raw material granules or thermoplastic combustible particles are pressed, and thus only a few spaces are present between the granules and the particles. As a result, spaces having a very small cross-sectional area tend to form, and an implant material comprising such spaces exhibits poor biocompatibility.

No particular limitation is imposed on the species of raw material granules which are employed in the present invention, but ceramic is preferable in consideration of biocompatibility. Raw material granules are preferably selected from the group consisting of alumina ceramic raw material, zirconia ceramic raw material, alumina-zirconia ceramic raw material, and calcium phosphate ceramic raw material (e.g., hydroxylapatite or tricalcium phosphate). The raw material granules may contain sintered additive components such as silica, magnesia, calcia, yttria, or glass components in addition to alumina and/or zirconia which is a primary component. A mixture of hydroxylapatite and tricalcium phosphate is more preferably employed as the raw material granules, since the mixture has excellent biocompatibility.

In the present invention, the final step is preferably carried out as follows. Firstly, a compact is heated to 200–500° C., and a thermoplastic combustible component present between raw material granules is burned out. Subsequently, the compact is heated to a predetermined firing temperature (e.g., 800–2,000° C.), intragranule binding and intergranule binding occur, and the compact is sintered, to thereby produce the desired biocompatible implant material. The firing temperature varies with the composition of the raw material which is employed. For example, in the case of alumina raw material, the firing temperature is 1,200–1,650° C.; in the case of zirconia raw material, the firing temperature is 1,110–1,800° C.; in the case of alumina zirconia raw material, the firing temperature is 1,200–1,700° C.; and in the case of calcium phosphate ceramic raw material, the firing temperature is 900–1,400° C. In each case, when the firing temperature is lower than the predetermined temperature, necks tend not to grow between particles, and thus a biocompatible implant material comprising a preferable particle-linkage structure is difficult to produce, which is unsatisfactory. In contrast, when the firing temperature is higher than the predetermined temperature, the particle-linkage structure thus produced tends to break, which is unsatisfactory.

In order to produce a preferable particle-linkage structure, for example, a mixture of glass powder and ceramic raw material powder serving as a primary component of a biocompatible implant material, the mixture being sinterable in a liquid phase, is preferably employed as raw material granules in the compacting step. A preferable example of such a mixture is a powder mixture of hydroxylapatite raw material powder and calcium phosphate glass powder. Through chemical reaction during firing, the glass powder disappears from the powder mixture, and tricalcium phosphate or a mixture of tricalcium phosphate and hydroxylapatite, which has excellent biocompatibility, is produced.

The invention will next be described in further detail by reference to the following Examples. However, the present invention should not be construed as being limited thereto.

EXAMPLE 1

Compacting Step:

A polyethylene oxide binder was added to a mixture of hydroxylapatite powder having a mean particle size of 0.6 $\mu$m and calcium phosphate glass frit (containing CaO-P$_2$O$_5$ in an amount of 90 mol % or more) (5 wt. %), to thereby prepare an aqueous slurry. The resultant slurry was granulated using a spray-drier, to prepare raw material granules having a spherical form. The granules were classified, to thereby obtain raw material granules having mean sizes of approximately 30 $\mu$m, 100 $\mu$m, 200 $\mu$m, and 300 $\mu$m. Separately, serving as thermoplastic combustible particles, spherical polyisobutyl methacrylate particles having mean sizes of 20 $\mu$m, 60 $\mu$m, 100 $\mu$m, and 300 $\mu$m were prepared. The particles were dry-mixed with the above-prepared granules at a predetermined ratio, to thereby obtain a powder mixture. The powder mixture was compacted at a pressure of 1–200 kg/cm$^2$ using a mold press, to thereby form a cuboid sample having a size of 60 mm×40 mm×50 mm.

Binding step:

The resultant compact was heated in a drier at 170° C. for three hours, to thereby melt spherical polyisobutyl methacrylate particles. Thereafter, the compact was allowed to cool, to thereby bind the raw material granules together via the polyisobutyl methacrylate that solidified after melting.

Shaping step:

After the compact was allowed to cool, the compact was subjected to shaping by use of a copy machining machine (MAKINO MILLING MACHINE CO., LTD., Model No. MSUN30) and also to drilling.

Final step:

After the shaping step, the compact was heated at a rate of 300° C./hour, and fired at 1,250° C. for three hours, to thereby produce a biocompatible implant material.

Tables 1 and 2 show in detail conditions for producing samples (Nos. 1 to 25) of Example 1 and the sample properties. In evaluation of "cutting" and "drilling" of each sample, when neither chips nor falling of particles were observed in the sample during shaping, a "good" rating was assigned, whereas when chips or falling of particles was observed in the sample during shaping, a "poor" rating was assigned. The results are shown in the tables. "Total pore percentage" of each sample was obtained through a known calculation method by measuring the absolute specific gravity and bulk specific gravity of the sample. The term "inter-pore size" refers to the pore size at the peak of the chart of the pore size distribution of each sample (see FIG. 1), the pore size distribution being measured by the mercury penetration method. The term "particle falling resistance" refers to a qualitative evaluation in which the strength of a sample is determined by observing whether or not particles fall when the sample is rubbed by the fingers.

TABLE 1

Example 1

| | Raw material granules | | | Thermoplastic combustible particles | | | Process (compacting, binding, shaping, final) | | | | | Properties | | |
|---|---|---|---|---|---|---|---|---|---|---|---|---|---|---|
| No. | Composition | Raw material size (μm) | Granule size (μm) | Material | Particle size (μm) | S1/S2 | Mixed amount (vol %) | Compacting pressure (kg/cm²) | Heating temperature (° C.) | Cutting | Drilling | Firing temperature (° C.) | Total pore percentage (%) | Inter-pore size (μm) | Particle falling resistance |
| 1 | Calcium phosphate | 0.6 | 30 | Iso-butyl methacrylate | 20 | 0.67 | 33 | 150 | 170 | Good | Good | 1,250 | 55 | 10 | Good |
| 2 | ↑ | ↑ | ↑ | ↑ | 60 | 2.00 | ↑ | ↑ | ↑ | ↑ | ↑ | ↑ | 56 | 15 | ↑ |
| 3 | ↑ | ↑ | ↑ | ↑ | 100 | 3.30 | ↑ | ↑ | ↑ | ↑ | ↑ | ↑ | 54 | 17 | ↑ |
| 4 | ↑ | ↑ | 60 | ↑ | 20 | 0.33 | ↑ | ↑ | ↑ | ↑ | ↑ | ↑ | 55 | 13 | ↑ |
| 5 | ↑ | ↑ | ↑ | ↑ | 60 | 1.00 | ↑ | ↑ | ↑ | ↑ | ↑ | ↑ | 54 | 18 | ↑ |
| 6 | ↑ | ↑ | ↑ | ↑ | 100 | 1.67 | ↑ | ↑ | ↑ | ↑ | ↑ | ↑ | 56 | 23 | ↑ |
| 7 | ↑ | ↑ | ↑ | ↑ | 200 | 3.30 | ↑ | ↑ | ↑ | ↑ | ↑ | ↑ | 55 | 25 | ↑ |
| 8 | ↑ | ↑ | ↑ | ↑ | 300 | 5.00 | ↑ | ↑ | ↑ | ↑ | ↑ | ↑ | 57 | 30 | ↑ |
| 9 | ↑ | ↑ | 100 | ↑ | 20 | 0.20 | ↑ | ↑ | ↑ | ↑ | ↑ | ↑ | 55 | 23 | ↑ |
| 10 | ↑ | ↑ | ↑ | ↑ | 60 | 0.60 | ↑ | ↑ | ↑ | ↑ | ↑ | ↑ | 57 | 28 | ↑ |
| 11 | ↑ | ↑ | ↑ | ↑ | 100 | 1.00 | ↑ | ↑ | ↑ | ↑ | ↑ | ↑ | 54 | 30 | ↑ |
| 12 | ↑ | ↑ | ↑ | ↑ | 200 | 2.00 | ↑ | ↑ | ↑ | ↑ | ↑ | ↑ | 56 | 33 | ↑ |
| 13 | ↑ | ↑ | ↑ | ↑ | 300 | 3.00 | ↑ | ↑ | ↑ | ↑ | ↑ | ↑ | 56 | 35 | ↑ |

*S1/S2 = (partial size)/(granule size)

TABLE 2

Example 1

| | Raw material granules | | | Thermoplastic combustible particles | | | Process (compacting, binding, shaping, final) | | | | | Properties | | |
|---|---|---|---|---|---|---|---|---|---|---|---|---|---|---|
| No. | Composition | Raw material size (μm) | Granule size (μm) | Material | Particle size (μm) | S1/S2 | Mixed amount (vol %) | Compacting pressure (kg/cm²) | Heating temperature (° C.) | Cutting | Drilling | Firing temperature (° C.) | Total pore percentage (%) | Inter-pore size (μm) | Particle falling resistance |
| 14 | Calcium phosphate | 0.6 | 200 | Iso-butyl methacrylate | 60 | 0.30 | 33 | 150 | 170 | Good | Good | 1,250 | 54 | 40 | Good |
| 15 | ↑ | ↑ | ↑ | ↑ | 100 | 0.50 | ↑ | ↑ | ↑ | ↑ | ↑ | ↑ | 56 | 48 | ↑ |
| 16 | ↑ | ↑ | ↑ | ↑ | 200 | 1.00 | ↑ | ↑ | ↑ | ↑ | ↑ | ↑ | 54 | 63 | ↑ |
| 17 | ↑ | ↑ | ↑ | ↑ | 300 | 1.50 | ↑ | ↑ | ↑ | ↑ | ↑ | ↑ | 55 | 70 | ↑ |

TABLE 2-continued

Example 1

| | Raw material granules | | | Thermoplastic combustible particles | | | | Process (compacting, binding, shaping, final) | | | | | Properties | | |
|---|---|---|---|---|---|---|---|---|---|---|---|---|---|---|---|
| No. | Composition | Raw material size (μm) | Granule size (μm) | Material | Particle size (μm) | S1/S2 | Mixed amount (vol %) | Compacting pressure (kg/cm²) | Heating temperature (° C.) | Cutting | Drilling | Firing temperature (° C.) | Total pore percentage (%) | Interpore size (μm) | Particle falling resistance |
| 18 | ↑ | ↑ | ↑ | ↑ | 200 | 1.00 | 20 | ↑ | ↑ | ↑ | ↑ | ↑ | 55 | 34 | ↑ |
| 19 | ↑ | ↑ | ↑ | ↑ | ↑ | ↑ | 40 | ↑ | ↑ | ↑ | ↑ | ↑ | 54 | 68 | ↑ |
| 20 | ↑ | ↑ | ↑ | ↑ | ↑ | ↑ | 33 | 5 | ↑ | ↑ | ↑ | ↑ | 60 | 70 | ↑ |
| 21 | ↑ | ↑ | ↑ | ↑ | ↑ | ↑ | ↑ | 50 | ↑ | ↑ | ↑ | ↑ | 58 | 67 | ↑ |
| 22 | ↑ | ↑ | ↑ | ↑ | ↑ | ↑ | ↑ | 200 | ↑ | ↑ | ↑ | ↑ | 50 | 58 | ↑ |
| 23 | ↑ | ↑ | 300 | ↑ | 100 | 0.33 | ↑ | 150 | ↑ | ↑ | ↑ | ↑ | 55 | 105 | ↑ |
| 24 | ↑ | ↑ | ↑ | ↑ | 200 | 0.67 | ↑ | ↑ | ↑ | ↑ | ↑ | ↑ | 57 | 112 | ↑ |
| 25 | ↑ | ↑ | ↑ | ↑ | 300 | 1.00 | ↑ | ↑ | ↑ | ↑ | ↑ | ↑ | 56 | 120 | ↑ |

*S1/S2 = (particle size)/(granule size)

In Example 1, a compact after the binding step was handled with ease, since raw material granules did not fall out. In the subsequent shaping step, even when the compact was subjected to shaping, chips did not occur in the compact. After the compact was shaped into an arbitrary form, a porous biocompatible implant material exhibiting no cracking was produced in the final step. The thus-produced implant material was subjected to X-ray diffraction for identification of crystal phases on the surface of the material. The results show that all the crystal phases were complex crystal phases of hydroxylapatite and tricalcium phosphate.

The pore size distribution of the biocompatible implant material was measured by the mercury penetration method. As a result, a number of pores having a size of some tens of μm were observed, and it was found that the material comprised spaces through which pores of large size three-dimensionally connect with one another and that spaces having an excessively small cross-sectional area were not formed (see FIG. 1). In addition, even when the biocompatible implant material was rubbed by the fingers, particles rarely fell from the material. Namely, the material had high strength and did not break during customary handling. FIG. 1 is a graph showing the pore size distribution of Sample No. 16. In FIG. 1, the peak in the vicinity of 1 μm is attributed to pores which are produced from primary particles (raw material powder) of ceramic.

Figure 2:
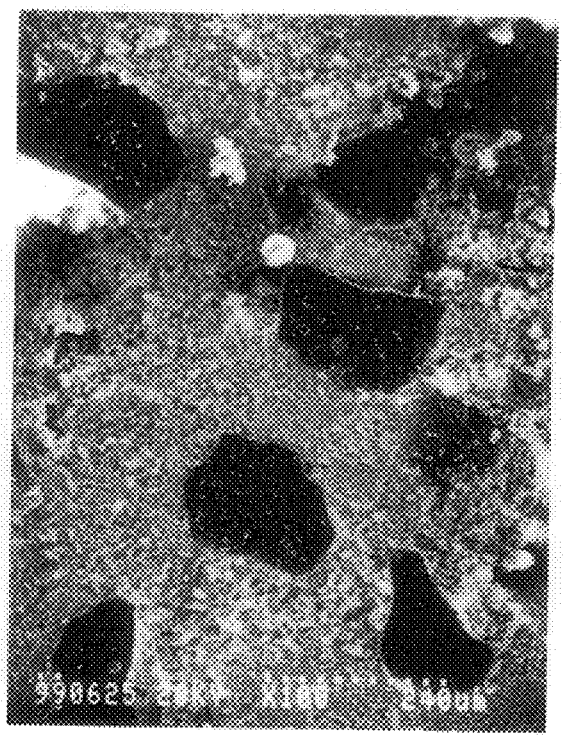
FIG. 2 is a cross-sectional SEM photograph of the compact of Example 1 (Sample No. 16 after the binding step).

FIG. 2 is a cross-sectional photograph of a compact after the binding step, which was taken using a scanning electron microscope (SEM). In the photograph, black regions represent thermoplastic combustible particles and other regions represent raw material granules. As is apparent from FIG. 2, raw material granules are brought into contact with one another not in point contact but in planar contact, and thermoplastic combustible particles adhere to the surrounding raw material granules after the particles are thermally deformed (or melted). As in the case of FIG. 1, FIG. 2 relates to Sample No. 16 and shows a photograph thereof.

The effects of Example 1 will next be described. It was confirmed that a compact after the binding step can be shaped into an arbitrary form which matches a lost portion of bone, and thus a porous biocompatible implant material having an arbitrary form, which is a final product, can be produced with ease. Since the compact was heated at an appropriate temperature, no liquid of excessively low viscosity flowed out of the compact after the thermoplastic combustible particles were melted, and thus the strength of the compact after the binding step was sufficiently enhanced. In addition, since the mean sizes of raw material particles and raw material granules, the size of thermoplastic combustible particles, and compacting pressure were appropriately determined, the raw material granules did not break during the compacting step, and the granules and the particles were almost closely packed. Therefore, a biocompatible implant material comprising spaces which do not have a very small cross-sectional area was finally produced, and the thus-produced biocompatible implant material is expected to have excellent biocompatibility in view of the inner structure of the material. Particularly, the biocompatible implant material comprises a mixture of hydroxylapatite and tricalcium phosphate, and thus the material has very excellent biocompatibility from the viewpoint of the properties of the material.

EXAMPLE 2

Compacting Step:

In the same manner as in Example 1, raw material granules formed of hydroxylapatite powder and calcium phosphate glass frit were prepared. The granules were classified, to thereby obtain raw material granules having mean sizes of approximately 30 μm, 100 μm, 200 μm, and 300 μm. Separately, serving as thermoplastic combustible particles, spherical low-density polyethylene particles having mean sizes of 40 μm, 180 μm, and 360 μm were prepared. The particles were dry-mixed with the above-prepared granules at a predetermined ratio, to thereby obtain a powder mixture. The powder mixture was compacted at a pressure of 1–200 kg/cm² using a mold press, to thereby form a cuboid sample having a size of 60 mm×40 mm×50 mm.

Binding Step:

The resultant compact was heated in a drier at 140° C. for three hours, to thereby melt the spherical low-density poly ethylene particles. Subsequently, the compact was allowed to cool, to thereby bind the raw material granules together via the low-density polyethylene that solidified after melting.

Shaping Step:

After the compact was allowed to cool, the compact was subjected to shaping by use of a copy machining machine and also to drilling.

Final Step:

After the shaping step, the compact was heated at a rate of 300° C./hour, and fired at 1,250° C. for three hours.

Table 3 shows in detail conditions for producing the samples (Nos. 26 to 28) of Example 2 and the sample properties.

Figure 4:
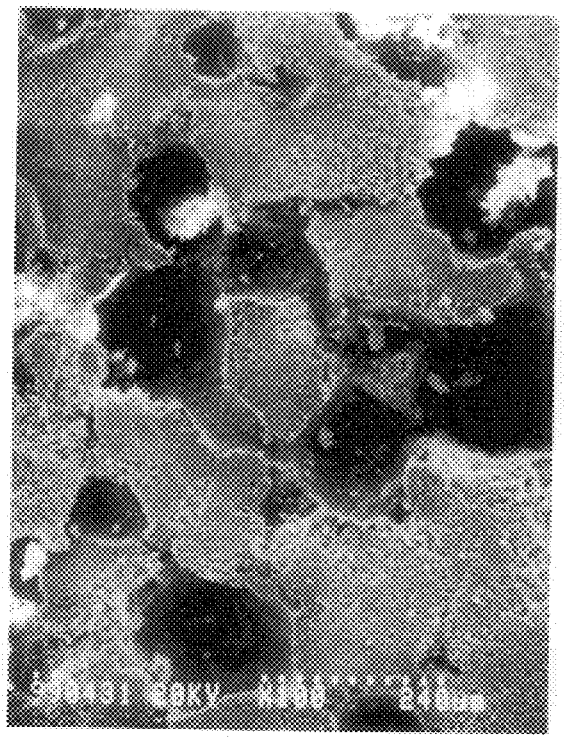
FIG. 4 is a cross-sectional SEM photograph of the compact of Example 2 (Sample No. 27 after the binding step).

FIG. 4 is a cross-sectional SEM photograph of a compact after the binding step. In the photograph, black regions represent thermoplastic combustible particles and other regions represent raw material granules. As is apparent from FIG. 4, thermoplastic combustible particles were once melted between raw material granules, and a portion of the

TABLE 3

Example 2 to 4

| | Raw material granules | | | Thermoplastic combustible particles | | | | Process (compacting, binding, shaping, final) | | | | | Properties | | |
|---|---|---|---|---|---|---|---|---|---|---|---|---|---|---|---|
| No. | Composition | Raw material size (μm) | Granule size (μm) | Material | Particle size (μm) | S1/S2 | Mixed amount (vol %) | Compacting pressure (kg/cm²) | Heating temperature (° C.) | Cutting | Drilling | Firing temperature (° C.) | Total pore percentage (%) | Inter-pore size (μm) | Particle falling resistance |
| 26 | Calcium phosphate | 0.6 | 200 | Iso-density polyethylene | 40 | 0.20 | 33 | 150 | 140 | Good | Good | 1,250 | 55 | 45 | Good |
| 27 | ↑ | ↑ | ↑ | ↑ | 180 | 1.90 | ↑ | ↑ | ↑ | ↑ | ↑ | ↑ | 56 | 63 | ↑ |
| 28 | ↑ | ↑ | ↑ | ↑ | 360 | 1.80 | ↑ | ↑ | ↑ | ↑ | ↑ | ↑ | 54 | 72 | ↑ |
| 29 | Alumina | 1.1 | ↑ | Iso-butyl methacrylate | 60 | 0.33 | 33 | ↑ | 170 | ↑ | ↑ | 1,550 | 54 | 35 | ↑ |
| 30 | ↑ | ↑ | ↑ | ↑ | ↑ | ↑ | 40 | ↑ | ↑ | ↑ | ↑ | ↑ | 67 | 50 | ↑ |
| 31 | ↑ | ↑ | ↑ | ↑ | 100 | 1.50 | 33 | ↑ | ↑ | ↑ | ↑ | ↑ | 53 | 38 | ↑ |
| 32 | ↑ | ↑ | ↑ | ↑ | ↑ | ↑ | 40 | ↑ | ↑ | ↑ | ↑ | ↑ | 69 | 55 | ↑ |
| 33 | ↑ | ↑ | ↑ | ↑ | 200 | 1.00 | 33 | ↑ | ↑ | ↑ | ↑ | ↑ | 55 | 43 | ↑ |
| 34 | ↑ | ↑ | ↑ | ↑ | ↑ | ↑ | 40 | ↑ | ↑ | ↑ | ↑ | ↑ | 68 | 65 | ↑ |
| 35 | Zirconia | 0.8 | ↑ | ↑ | 60 | 0.33 | 33 | ↑ | ↑ | ↑ | ↑ | 1,450 | 55 | 34 | ↑ |
| 36 | ↑ | ↑ | ↑ | ↑ | ↑ | ↑ | 40 | ↑ | ↑ | ↑ | ↑ | ↑ | 66 | 52 | ↑ |
| 37 | ↑ | ↑ | ↑ | ↑ | 100 | 1.50 | 33 | ↑ | ↑ | ↑ | ↑ | ↑ | 54 | 42 | ↑ |
| 38 | ↑ | ↑ | ↑ | ↑ | ↑ | ↑ | 40 | ↑ | ↑ | ↑ | ↑ | ↑ | 70 | 57 | ↑ |
| 39 | ↑ | ↑ | ↑ | ↑ | 200 | 1.00 | 33 | ↑ | ↑ | ↑ | ↑ | ↑ | 55 | 43 | ↑ |
| 40 | ↑ | ↑ | ↑ | ↑ | ↑ | ↑ | 40 | ↑ | ↑ | ↑ | ↑ | ↑ | 67 | 65 | ↑ |

*Nos. 28 to 28: Example 2, Nos. 29 to 34: Example 3,
Nos. 35 to 40: Example 4, S1/S2 = (particles size)/(granule size)

In Example 2, a compact after the binding step was handled with ease, since raw material granules did not fall out. In the subsequent shaping step, even when the compact was subjected to shaping, chips did not occur in the compact. After the compact was shaped into an arbitrary form, a porous biocompatible implant material exhibiting no cracking was produced in the final step. The thus-produced biocompatible implant material was subjected to X-ray diffraction for identification of crystal phases on the surface of the material. The results showed that all the crystal phases were complex crystal phases of hydroxylapatite and tricalcium phosphate.

Figure 3:
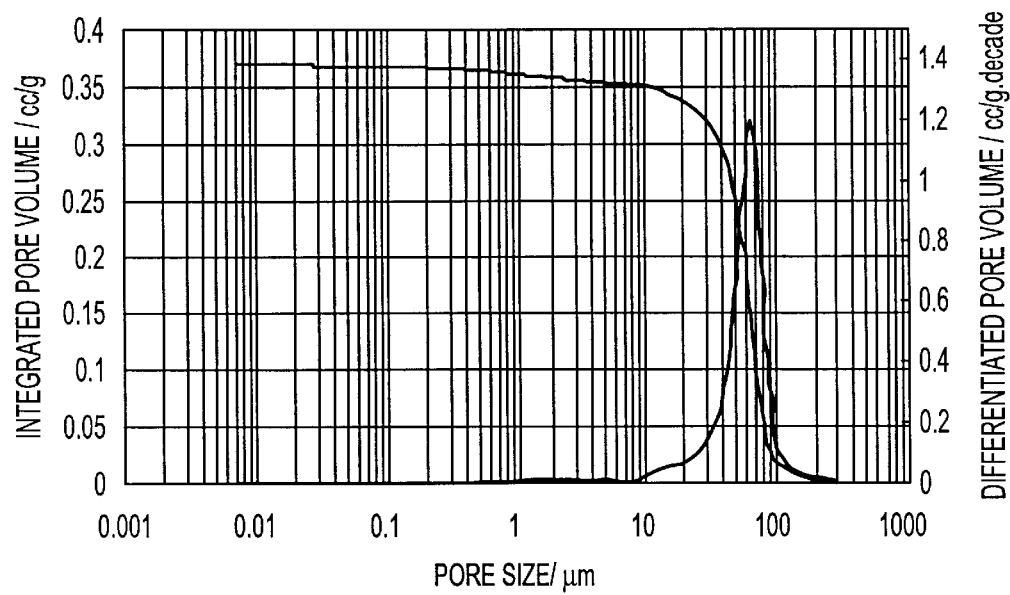
FIG. 3 is a chart showing the pore size distribution curve of the biocompatible implant material of Example 2 (Sample No. 27).

The pore size distribution of the biocompatible implant material was measured by the mercury penetration method. As a result, a number of pores having a size of some tens of μm were observed, and it was found that the material comprises spaces through which pores of large size three-dimensionally connect with one another and that spaces having a very small cross-sectional area were not formed (see FIG. 3). In addition, even when the biocompatible implant material was rubbed by the fingers, particles rarely fell from the material. Namely, the material had high strength and did not break during customary handling. FIG. 3 is a graph showing the pore size distribution of Sample No. 27.

thermoplastic combustible particles entered spaces between the granules, and then the particles were solidified. As in the case of FIG. 3, FIG. 4 relates to Sample No. 27 and shows a photograph thereof.

The effects of Example 2 were similar to those of Example 1.

EXAMPLE 3

The procedure of Example 1 was repeated, except that the raw material powder was replaced by alumina ceramic raw material powder having a mean particle size of 1.1 μm, to thereby produce a biocompatible implant material. Table 3 shows in detail conditions for producing samples (Nos. 29 to 34) of Example 3 and the sample properties. In Example 3, the biocompatible implant material comprised a packing linkage structure in which alumina ceramic particles having a size of approximately 20–80 μm were packed and linked together, and lost portions of the packed particles were observed in the structure. In the biocompatible implant material, there were pores having a size of some tens of μm, which were formed by three-dimensional linkage of the lost portions. The effects of Example 3 were similar to those of Example 1.

EXAMPLE 4

The procedure of Example 1 was repeated, except that the raw material powder was replaced by zirconia ceramic raw material powder having a mean particle size of 0.8 μm, to thereby produce a biocompatible implant material. Table 3 shows in detail conditions for producing samples (Nos. 35 to 40) of Example 4 and the sample properties. In Example 4, the biocompatible implant material comprised a packing linkage structure in which zirconia ceramic particles having a size of approximately 20–80 μm were packed and linked together, and lost portions of the packed particles were observed in the structure. A biocompatible implant material of zirconia ceramic was produced comprising pores having a size of some tens of μm, which were formed by three-dimensional linkage of the lost portions. The effects of Example 4 were similar to those of Example 1.

COMPARATIVE EXAMPLE 1

Compacting Step:

In the same manner as in Example 1, raw material granules formed of hydroxylapatite powder and calcium phosphate glass frit were prepared. The granules were classified, to thereby obtain raw material granules having a mean size of approximately 100 μm. Separately, spherical polymethyl methacrylate (PMMA) particles having sizes of 20 μm, 60 μm, 100 μm, 200 μm, and 300 μm were prepared. The particles were dry-mixed with the above-prepared granules at a predetermined ratio, to thereby obtain a powder mixture. The powder mixture was compacted at a pressure of 150 kg/cm² using a mold press, to thereby form a cuboid sample having a size of 60 mm×40 mm×50 mm. The spherical PMMA particles have a three-dimensional linkage structure which is formed using a cross-linking agent. The PMMA particles are not thermoplastic particles.

Binding Step:

The binding step was not carried out.

Shaping Step:

The resultant compact was subjected to cutting and drilling, but the compact was broken and could not be shaped into an arbitrary form. Therefore, the final step could not be carried out.

Table 4 shows in detail conditions for producing samples (Nos. 41 to 45) of Comparative Example 1 and the sample properties. As is apparent from the above results, when the binding step is not carried out, a compact does not attain a strength such that the compact can be shaped, and thus biocompatible implant materials of various forms cannot be produced with ease.

TABLE 4

Comparative Examples 1 and 2

| | Raw material granules | | | Thermoplastic combustible particles | | | Process (compacting, binding, shaping, final) | | | | Properties | | | |
|---|---|---|---|---|---|---|---|---|---|---|---|---|---|---|
| No. | Composition | Raw material size (μm) | Granule size (μm) | Material | Particle size (μm) | S1/S2 | Mixed amount (vol %) | Compacting pressure (kg/cm²) | Heating temperature (° C.) | Cutting | Drilling | Firing temperature (° C.) | Total pore percentage (%) | Inter-pore size (μm) | Particle falling resistance |
| 41 | Calcium phosphate | 0.6 | 100 | PMMA | 20 | 0.20 | 33 | 150 | — | Poor | Poor | — | — | — | — |
| 42 | ↑ | ↑ | ↑ | ↑ | 60 | 0.60 | ↑ | ↑ | — | ↑ | ↑ | — | — | — | — |
| 43 | ↑ | ↑ | ↑ | ↑ | 100 | 1.00 | ↑ | ↑ | — | ↑ | ↑ | — | — | — | — |
| 44 | ↑ | ↑ | ↑ | ↑ | 200 | 2.00 | ↑ | ↑ | — | ↑ | ↑ | — | — | — | — |
| 45 | ↑ | ↑ | ↑ | ↑ | 300 | 3.00 | ↑ | ↑ | — | ↑ | ↑ | — | — | — | — |
| 46 | ↑ | ↑ | ↑ | ↑ | 20 | 0.20 | ↑ | ↑ | 170 | ↑ | ↑ | — | — | — | — |
| 47 | ↑ | ↑ | ↑ | ↑ | 60 | 0.60 | ↑ | ↑ | ↑ | ↑ | ↑ | — | — | — | — |
| 48 | ↑ | ↑ | ↑ | ↑ | 100 | 1.00 | ↑ | ↑ | ↑ | ↑ | ↑ | — | — | — | — |
| 49 | ↑ | ↑ | ↑ | ↑ | 200 | 2.00 | ↑ | ↑ | ↑ | ↑ | ↑ | — | — | — | — |
| 50 | ↑ | ↑ | ↑ | ↑ | 300 | 3.00 | ↑ | ↑ | ↑ | ↑ | ↑ | — | — | — | — |
| 51 | ↑ | ↑ | 200 | ↑ | 60 | 0.30 | ↑ | ↑ | ↑ | ↑ | ↑ | — | — | — | — |
| 52 | ↑ | ↑ | ↑ | ↑ | 100 | 0.50 | ↑ | ↑ | ↑ | ↑ | ↑ | — | — | — | — |
| 53 | ↑ | ↑ | ↑ | ↑ | 200 | 1.00 | ↑ | ↑ | ↑ | ↑ | ↑ | — | — | — | — |
| 54 | ↑ | ↑ | ↑ | ↑ | 300 | 1.50 | ↑ | ↑ | ↑ | ↑ | ↑ | — | — | — | — |

*Nos. 41 to 45; Comp. Ex. 1, Nos. 46 to 54: Comp. Ex. 2
S1/S2 (particle size)/(granule size)

COMPARATIVE EXAMPLE 2

Compacting Step:

In the same manner as in Example 1, raw material granules formed of hydroxylapatite powder and calcium phosphate glass frit were prepared. The granules were classified, to thereby obtain raw material granules having mean sizes of approximately 100 μm and 200 μm. Separately, spherical PMMA particles having sizes of 20 μm, 60 μm, 100 μm, 200 μm, and 300 μm were prepared. The particles were dry-mixed with the above-prepared granules at a predetermined ratio, to thereby obtain a powder mixture. The powder mixture was compacted at a pressure of 150 kg/cm² using a mold press, to thereby form a cuboid sample having a size of 60 mm×40 mm×50 mm. In the same manner as in Comparative Example 1, the spherical PMMA particles have a three-dimensional linkage structure which is formed using a cross-linking agent. The PMMA particles are not thermoplastic particles.

Binding Step:

The resultant compact was heated in a drier at 170° C. for five hours, and then allowed to cool. During heating, the compact was not softened or melted.

Shaping Step:

The resultant compact was subjected to cutting and drilling, but the compact was broken and could not be shaped into an arbitrary form. Therefore, the final step could not be carried out. Table 4 shows in detail conditions for producing samples (Nos. 46 to 54) of Comparative Example 2 and the sample properties. As is apparent from the above results, in the case in which thermoplastic combustible particles are not softened and melted even when heated, a compact after the binding step does not have a strength such that the compact can be shaped, and thus biocompatible implant materials of various forms cannot be produced with ease.

While the invention has been described in detail and with reference to specific embodiments thereof, it will be apparent to one skilled in the art that various changes and modifications can be made therein without departing from the spirit and scope thereof.

This application is based on Japanese Patent Application No. Hei. 11-226675 filed Aug. 10, 1999, which is incorporated herein by reference in its entirety.

What is claimed is:

1. A process for producing a biocompatible implant material, which comprises:

a compacting step which comprises compacting a mixture of sinterable raw material granules and thermoplastic combustible particles to thereby obtain a compact;

a binding step which comprises heating the compact to the softening point of the thermoplastic combustible particles or higher to thereby thermally deform or melt the particles between the raw material granules, and then cooling the compact to thereby solidify the deformed or melted particles, for binding the raw material granules together;

a shaping step which comprises shaping the bound compact into an arbitrary form; and a final step which comprises burning out the thermoplastic combustible particles present between the raw material granules and sintering the granules, to thereby produce a porous biocompatible implant material.

2. The process for producing a biocompatible implant material according to claim 1, wherein the binding step comprises heating the compact at a temperature such that the thermoplastic combustible particles do not melt and flow out from the compact.

3. The process for producing a biocompatible implant material according to claim 1, wherein the compacting step comprises compacting the powder mixture at a pressure such that the raw material granules do not break and the granules are packed at a substantially highest density.

4. The process for producing a biocompatible implant material according to claim 1, wherein the compacting step comprises compacting a mixture of raw material granules having a granule size of 10–800 $\mu$m formed from a powder having a mean particle size of 5 $\mu$m or less and thermoplastic combustible particles having a particle size of 2–1,600 $\mu$m at a pressure of 1–200 kg/cm$^2$.

5. The process for producing a biocompatible implant material according to claim 1, wherein in the compacting step, the raw material granules are selected from the group consisting of alumina ceramic raw material, zirconia ceramic raw material, alumina-zirconia ceramic raw material and calcium phosphate ceramic raw material.

6. The process for producing a biocompatible implant material according to claim 1, wherein the binding step comprises heating the compact at a temperature between the softening point and the melting point of the thermoplastic combustible particles.

7. The process for producing a biocompatible implant material according to claim 1, wherein the raw material granules comprise a mixture of hydroxylapatite powder and calcium phosphate glass frit and the thermoplastic combustible particles comprise polyisobutyl methacrylate.

* * * * *